United States Patent
Groth et al.

(10) Patent No.: US 6,443,889 B1
(45) Date of Patent: Sep. 3, 2002

(54) PROVISION OF DECISION SUPPORT FOR ACUTE MYOCARDIAL INFARCTION

(76) Inventors: Torgny Groth, Döbelnsgatan 24A, SE-752 37 Uppsala (SE); Johan Ellenius, Geijersgatan 15B, SE-752 26 Uppsala (SE)

( * ) Notice: Subject to any disclaimer, the term of this patent is extended or adjusted under 35 U.S.C. 154(b) by 0 days.

(21) Appl. No.: 09/501,233

(22) Filed: Feb. 10, 2000

(51) Int. Cl.$^7$ ................................................ A61B 5/00
(52) U.S. Cl. .......................... 600/300; 128/925; 706/15
(58) Field of Search ................................. 128/920, 921, 128/922, 923, 924, 925; 706/15, 16; 600/300, 515

(56) References Cited

U.S. PATENT DOCUMENTS 5,515,477 A * 5/1996 Sutherland .................. 128/925
5,690,103 A 11/1997 Groth et al.

OTHER PUBLICATIONS

Baxt, William G. M.D., Use of an Artificial Neural Network for the Diagnosis of Myocardial Infarction, Dec. 1991, Annals of Internal Medicine, vol. 15, No. 11, pp 843–848.*
Ellenius, Johan, Early Assessment of Patients with Suspected Acute Myocardial Infarction by Biochemical Monitoring and Neural Network Analysis, 1997, Clinical Chemistry, vol. 43, No. 10, pp 1919–1925.*
Jorgenssen et al. "Clinical Chemistry", vol. 42, No. 4, pp. 604–612, (1996).
Held et al., "IEEE Transactions On Biomedical Engineering," vol. 47, No. 1, pp. 115–123, Jan. 2000.
Ornes et al., "A Visual Neural Network that Learns Perceptual Relationships," vol. 1, pp. 873–875, 1998.
Sunemark et al. "Computers and Biomedical Research," vol. 31, pp. 59–69, 1998.
Ulug. "IEEE International Conference on Neural Networks," vol. 3, pp. 1662–1667, 1994.
Setiono et al. "Neurocomputing," No. 17, pp. 1–24, 1997.
Elenius et al. "International Journal of Medical Informatics," No. 57, pp. 181–202, 2000.

* cited by examiner

*Primary Examiner*—Eric F. Winakur
*Assistant Examiner*—David McCrosky
(74) *Attorney, Agent, or Firm*—Young & Thompson (57) ABSTRACT

The present invention provides methods and apparatuses, which make use of at least one trained and tuned artificial neural network (16) to generate decision regions (32) in the n-dimensional space of n input variables associated with AMI. The set of measured variables (30) is related to the decision regions (32), in order to provide decision support. Preferably, the decision regions (32) are graphically visualized as areas in a two-dimensional diagram. Preferably, the artificial neural network (16) is trained by patient specific parameters. The variables associated with AMI (30) are preferably selected as biochemical markers and/or quantities derived from continuous/intermittent ECG/VCG. The performance of the artificial neural network (16) is preferably optimally tuned to clinical requirements on predictive values of the artificial neural network output in given prevalence situations.

32 Claims, 11 Drawing Sheets

PRIOR ART

Fig. 1a

PRIOR ART

PROVISION OF DECISION SUPPORT FOR ACUTE MYOCARDIAL INFARCTION

TECHNICAL FIELD

The present invention relates to the assessment, management and treatment of patients with suspected acute myocardial infarction (AMI), and more particularly to methods and apparatuses for decision support intended for early assessment of such patients with regard to classification into groups related to different preferred management and treatment options.

BACKGROUND

An early assessment within the first hours after onset of symptoms is essential for the optimal management and treatment of patients with suspected acute myocardial infarction (AMI) as has been documented by e.g. the National Heart Attack Alert Program Coordinating Committee, 60 minutes to Treatment Working Group (in Ann Emerg Med 1994; 23:311–329). In patients with ST-elevation in their initial ECG recording on admission the diagnosis is straight forward. Moreover, the total sum of ST-elevations in all ECG-leads gives a good estimate of the myocardium at risk. However, in at least 40% of patients with AMI the 12-lead ECG is non-diagnostic on admission. In these patients the diagnosis has to be based on clinical data and measurements of biochemical markers, until recently a time consuming procedure that causes a delay in starting the treatment. An early and reliable prediction of the infarct size is also difficult for this group of patients. In the heterogeneous group of patients admitted to the hospital because of chest pain, considerable economic gains might be achieved by early identification of those patients (approximately 60–70%) who are at sufficiently low risk of AMI and its complications to be transferred to a general ward outside the coronary care unit (CCU). Among patients with unstable angina 30–50% have minor elevations of sensitive biochemical markers such as creatine kinase MB and troponin-T. The term minor myocardial damage (MMD) has been proposed for these minor elevations. Since MMD indicates an increased risk of future cardiac events it seems important not only to detect AMI, but also to detect MMD as early as possible.

Thus, in the early management of patients with acute chest pain and with non-diagnostic ECG at admission, there are several important issues to be addressed in order to take suitable actions. The existence of an AMI has to be determined. If an AMI is present, the ultimate infarct size is useful to know for the continued treatment. The time when the infarction actually occurred is also important. If the patient does not have an AMI, it is still useful to decide if the patient have a high or low risk for subsequent cardiac events. The clinician has to consider the patient's history and physical status, the results of ECG and blood tests etc. This evaluation process may be time consuming and is heavily dependent on the clinician's knowledge and experience. The biochemical measurement results form an important basis on which the future management of the patient relies.

There are important differences in the kinetic properties of the biochemical markers of AMI of today, e.g. myoglobin, CKMB and cardiac troponin-T. All these markers are indicative of AMI, however, on different time scales. Myoglobin has a rather quick response, while at least troponin-T has a much slower appearance rate. A combination of measurements of more than one marker is necessary.

Computer methods using artificial neural networks have been applied for AMI detection based on clinical data, measurements of biochemical markers and ECG/VCG parameters. Jörgensen et al, Clin. Chem. 1996, vol. 42(4), pp. 604–612 and 613–617, investigated the diagnostic performance of neural networks trained on various combinations of initial ECG data, and serum concentrations of CKB, LD1 and potassium, on admission, 12 and 24 hours after admission. In a recent paper (Comp. Biomed. Research 1998, vol. 36, 59–69) Sunemark et al investigated an approach to serial VCG/ECG analysis based on artificial neural networks combining two ECG and VCG measurements. In short, the neural network applications by Sunemark et al and Jörgensen et al have not addressed the problem of early AMI size predicition in chest pain patients with non-diagnostic ECG on admission.

In U.S. Pat. No. 5,690,103, methods and apparatuses for detection or exclusion of acute myocardial infarction using artificial neural network (ANN) analysis of measurements of biochemical markers are disclosed. The overall invention categorizes patients with suspected AMI with regard to AMI/non-AMI; infarct size; time since onset of infarction; and non-AMI with/without minor myocardial damage (MMD). The categorization is generally based on frequent blood sampling during the first hours after admission and measurement of selected biochemical markers of AMI with different rates of appearance in circulating blood. The computations are performed by using specially designed artificial neural networks. Early detection/exclusion of acute myocardial infarction is provided, generally within 3 hours from admission of the patient. Furthermore, early prediction of the "major infarct size" and early estimation of the time from onset are also provided.

It is important to understand that the time aspect is very crucial in the present technical field. After 12–24 hours after admission, the patterns of the marker concentrations are generally so pronounced that the clinicians themselves can easily assess AMI therefrom without using any type of neural network support. However, 12 hours after admission, the potential benefit of e.g. thrombolytic treatment has decreased to a very low level. Measurement evaluation and decisions have to be made in the very first hours after admission of a patient.

The methods and apparatuses of the above U.S. patent provide a large development in providing early and reliable detection, prediction and estimation in connection with AMI. Although the new technology of the above patent has worked in a satisfactory manner, there still remain issues that should be addressed regarding the incorporation of these types of artificial neural networks into a medical decision support system, and the transferability of such a system to function in a new environment with its specified medical requirements.

SUMMARY

A general objective of the present invention is to further improve the quality of the decision support for early assessment of patients with suspected acute myocardial infarction (AMI), derived by using artificial neural networks. A further objective of the present invention is to relate measured variables associated with AMI to regions of AMI classification groups related to management options and treatment procedures, and in particular to visualize such relations in an informative way. Another objective of the present invention is to provide artificial neural networks, which are tuned to fulfil clinical requirements on the certainty of predicted infarct size and corresponding AMI classification groups in various prevalence situations. Yet another objective of the present invention is to provide artificial neural networks that make use of variables associated with AMI, which are derived from intermittent and/or continuous ECG/VCG measurements.

The above objectives are accomplished by methods and apparatuses according to the appended claims.

In general words, one aspect of the present invention provides a method and an apparatus, which make use of at least one trained and tuned artificial neural network to generate decision regions in the n-dimensional space of n input variables associated with AMI. The set of measured variables at a certain time instance, i.e. a point in the n-dimensional space, is related to the decision regions, in order to provide decision support. Preferably, these decision regions are projected and graphically visualized as areas in a parameterized two-dimensional diagram, with two major variables as independent variables. The values of the remaining n−2 input variables are the corresponding parameters. Preferably, the two major variables are biochemical AMI markers. The position of the point representing a present set of values of the selected measured variables displayed in the diagram gives an easily interpreted indication of a recommended classification and also gives information on the closeness to neighboring decision regions. Preferably, the artificial neural network is trained with use of sets of measurements of variables associated with AMI at a certain time instance as well as patient specific parameters.

According to another aspect, the present invention provides a method and an apparatus, which provides at least one artificial neural network that is capable to generate decision support based on n input variables associated with AMI. The performance of the artificial neural network is optimally tuned to clinical requirements on predictive values of the artificial neural network based classification in given prevalence situations.

According to yet another aspect, the present invention provides a method and an apparatus, which make use of at least one trained artificial neural network to generate decision support based on n input variables associated with AMI. At least one of the variables associated with AMI is derived from intermittent/continuous ECG/VCG recordings.

It is important to understand that the invention relates to decision support for the management of patients with suspected acute myocardial infarction, a decision support that may be used by a nurse and/or a clinician in the assessment of such a patient.

BRIEF DESCRIPTION OF THE DRAWINGS

The invention, together with further objectives and advantages thereof, may best be understood by making reference to the following description taken together with the accompanying drawings, in which:

FIG. 1b is a schematic illustration of the use of an artificial neural network of FIG. 1a;

FIG. 3b is a schematic illustration of the use of the trained and tuned artificial neural network of FIG. 3a;

DETAILED DESCRIPTION

In the early assessment and management of patients with acute chest pain, there are different standard measures to take. Upon admission, the patient is normally investigated by an initial ECG/VCG (Electrocardiogram/vectorcardiogram measurement. However, for many patients, the ECG is non-diagnostic on admission, even if an AMI is present. In that case biochemical monitoring is required. The clinician has further to consider the age and sex of the patient, the patient's history of diseases and present physical status, e.g. if the patient belongs to any risk groups, such as smokers or diabetics. Furthermore, a series of biochemical tests are normally performed, e.g. tests on circulating blood. In the blood, the concentrations of biochemical markers of AMI are of particular interest. Such blood tests may be repeated intermittently, giving a time series of biochemical marker concentrations. In most cases, the patients are also connected to a continuous ECG or VCG monitoring systems. A clinician has to make decisions about management of the patient as soon as possible based on the available information. This decision-making process may be time consuming and is heavily dependent on the clinician's knowledge and experience. In order to start any relevant treatments of the patient, the time aspect is extremely important. Several hours after admission, the complete knowledge of measured concentrations of biochemical markers etc. may give an almost full description of the situation of the patient, but if no treatment has already been initiated, the potential benefit of such treatment is often very low at this point.

In the present invention, the term artificial neural network (ANN) refers to a computational structure, which is trained on a representative set of pre-classified example cases. In use, the neural network is applied for classification of unknown cases. Additional background on neural network classification can be obtained by reviewing "Neural networks and related methods for classification" by Ripley B. D., in J. R. Statist. Soc. B 1994; 56(3): pages 409–456.

Figure 1A:
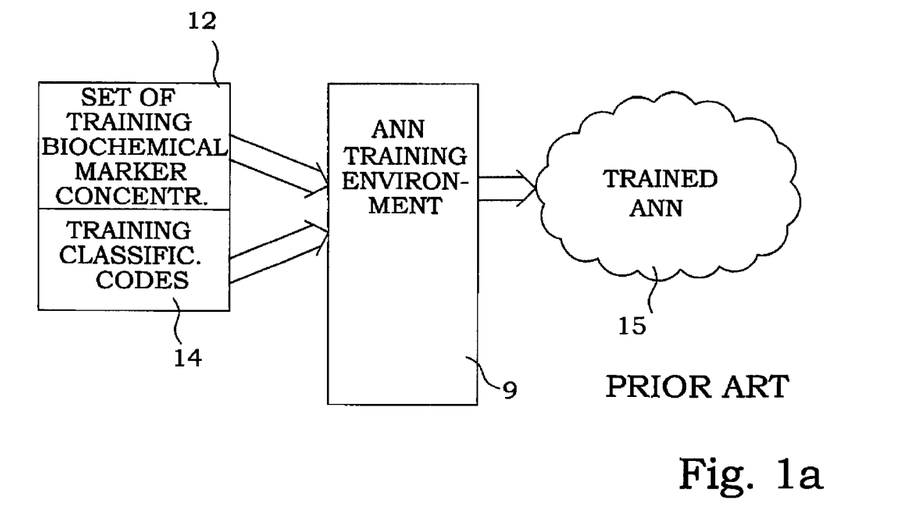
FIG. 1a is a schematic illustration of a training process of an artificial neural network according to prior art.

In U.S. Pat. No. 5,690,103, an artificial neural network is used for early detection/exclusion, prediction and estimations of AMI related characteristics. U.S. Pat. No. 5,690,103 is hereby incorporated by reference in its entirety. FIG. 1a illustrates the training process of an artificial neural network according to U.S. Pat. No. 5,690,103. A training set with concentration measurements of biochemical markers 12 of AMI are used to train the artificial neural network in a training environment 9. The training set 12 is associated with a training classification code 14 of e.g. AMI/non-AMI. The trained artificial neural network 15 will then respond to a corresponding set of biochemical markers to generate a classification of the patient.

Figure 1B:
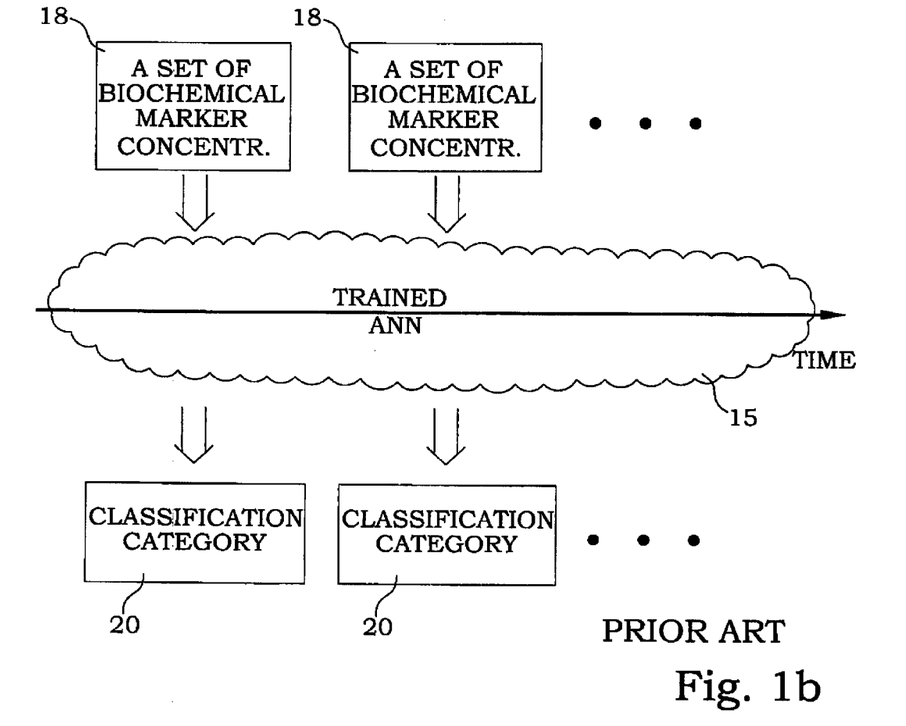

FIG. 1b illustrates the trained artificial neural network 15 of FIG. 1a in use. Successive sets of concentration measurements of biochemical markers of AMI 18 are entered as input to the trained artificial neural network 15. The output will give the most probable classification 20 of the patient given the available information. With the classification given above, the outcome could be an indication of AMI, an indication of non-AMI or an indication of "uncertain state" requiring further measurements.

Figure 2A:
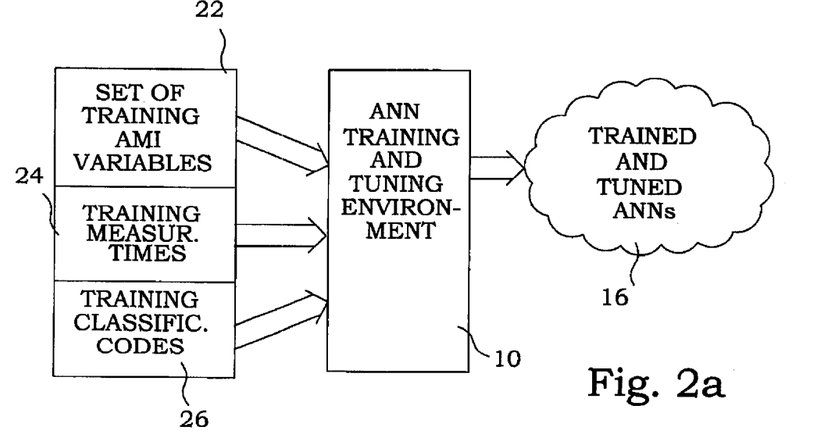
FIG. 2a is a schematic illustration of a training and tuning process of an artificial neural network used in the present invention.

In FIG. 2a, the training of artificial neural networks used in the present invention is illustrated. An artificial neural network 16 is trained in a training and tuning environment 10 with use of a training set of variables associated with AMI 22 and their corresponding measuring times 24. Each case in the training set is preclassified and labeled with a patient classification code 26. This classification can be performed in many ways, preferably based on AMI characteristics related to clinical classification, management options or treatment procedures. The trained artificial neural network 15 is tuned in a procedure described in FIG. 2c. Prevalence and clinical requirement specifications 13 are used on a trained ANN 15 in a tuning procedure 11 to form a trained and tuned ANN 16. A preferred procedure to perform this tuning is presented below.

Figure 2B:
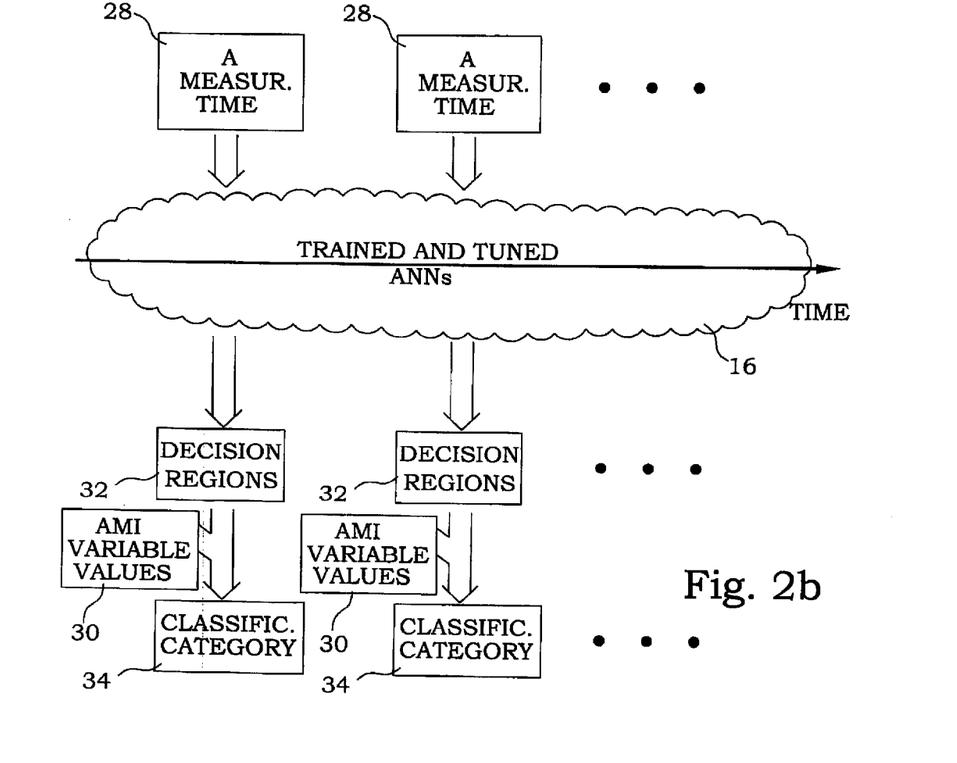
FIG. 2b is a schematic illustration of the use of a trained and tuned artificial neural network according to the present invention.

The use of a trained and tuned artificial neural network 16 according to the present invention provides ANN-based decision algorithms and is schematically illustrated in FIG. 2b. In use of the trained and tuned artificial neural networks 16, successive sets of AMI variables 30 based on or derived from measurements of variables associated with AMI are provided for the patient under investigation. These sets 30 of variables are associated with a certain measurement time 28, which is entered into the trained and tuned artificial neural networks 16. The trained artificial neural networks 16 generate decision regions 32 expressed in the space of the variables associated with AMI. The decision regions 32 correspond to the classification codes of the training set. The decision regions 32 are preferably graphically visualized in two-dimensional diagrams. This visualization will be discussed more in detail below. The variable values 30 of the patient under present investigation are related to the regions 32, which give an indication of which classification 34 the present patient should be referred to. Furthermore, the position of the "measurement point" representing the variable values 30, with respect to neighboring decision regions, gives information about the certainty of the categorization. The explicit generation of the decision regions 32 thus gives useful additional information.

There are ANN structures, e.g. the multiple-single layer perceptron, which do not handle time explicitly. In such a case, the measurement time is not necessary to enter.

Figure 3A:
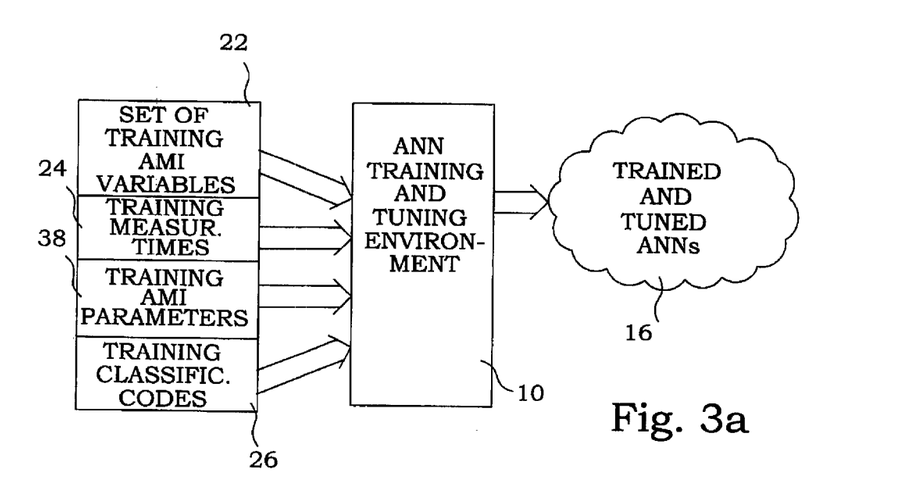
FIG. 3a is a schematic illustration of a training and tuning process of another artificial neural network used in the present invention.
Figure 3B:
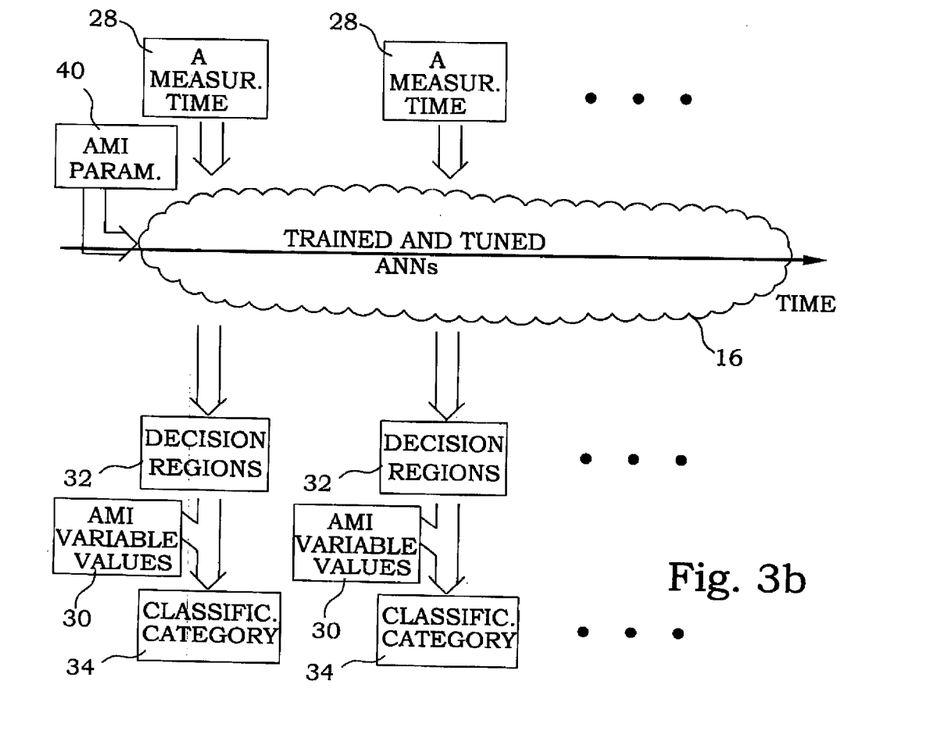

In an alternative embodiment, illustrated in FIG. 3a, the artificial neural networks 10 are additionally trained with use of patient specific AMI parameters 38, e.g. parameters derived from measurements of initial ECG/VCG, age, sex, risk factors, present health status or history of diseases. Risk factors may be related e.g. to smoking or diabetes. These AMI parameters 38 are valid throughout the entire time series of measurement sets of AMI variables. In use, as illustrated in FIG. 3b, the same type of AMI-parameters 40 are measured for the patient under investigation. The measured AMI parameters 40 are provided to the trained and tuned artificial neural networks 16 as input parameters valid throughout the whole period of investigation. The decision regions 32, generated by the artificial neural networks 16, then also depend on the values of these patient specific parameters 40.

Figure 3C:
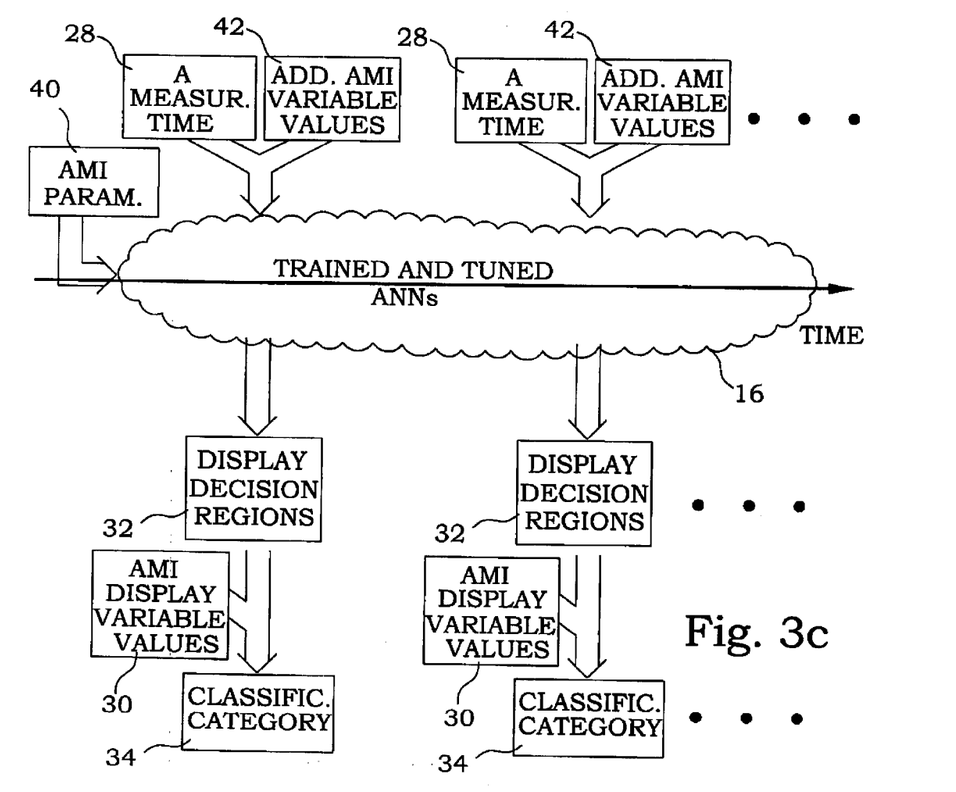
FIG. 3c is a schematic illustration of the preferred use of a trained and tuned artificial neural network according to the present invention.

In a preferred embodiment of FIG. 3c with regard to visualization, only 2 AMI variables, so called AMI display variables, are used for spanning a display diagram, in which the decision regions are visualized. The other additional n−2 AMI variables 42 and AMI parameters 40, discussed above, are used to generate the actual visualized decision regions. In use, the additional AMI variables 42 and AMI parameters 40 are measured and provided to the trained and tuned artificial neural networks 16 in order to specify the relevant decision regions 32 to be generated in the individual case at a specific measurement time. In other words, a number of decision regions are visualized in a two-dimensional diagram defined by coordinates of two of the AMI variables. The values of the two variables are presented as a point in the two-dimensional diagram. The values of the remaining n−2 AMI variables and parameters at the same time point are used for generating the decision regions.

The classification codes 26 of the training sets and the related decision 32 regions may be based on various considerations. Preferably, the grouping should have a close connection with management or clinical aspects. One possible categorization is to classify patients in groups with "non-AMI", "minor AMI", "medium AMI" and "major AMI". Regarding AMI variables comprising biochemical markers for AMI, a patient may during monitoring e.g. be classified as having "at least a minor AMI" if the peak concentration of P-CKMB is predicted to exceed 2 URL units (upper reference limit units), "at least a medium AMI" if the peak concentration of P-CKMB is predicted to exceed 5 URL units, and a "major" AMI if the peak concentration of P-CKMB is predicted to exceed 10 URL units. Otherwise the patient is classified as having a "non-AMI" or being "uncertain" until e.g. a predefined time has elapsed from the initial measurement. Such decision regions are of interest for the clinician in deciding an appropriate management of the patient.

Other classification groups are also possible. The patients of the training sets could e.g. be grouped with regard to which treatment that is regarded to be appropriate.

It is also possible to train and tune different artificial neural networks on the same sets of variables, but with different classification codes. Such ANNs may then be used in parallel. The clinician using the system may then select the set of decision regions he/she wants to use, depending on the individual skill and experience.

Figure 4A:
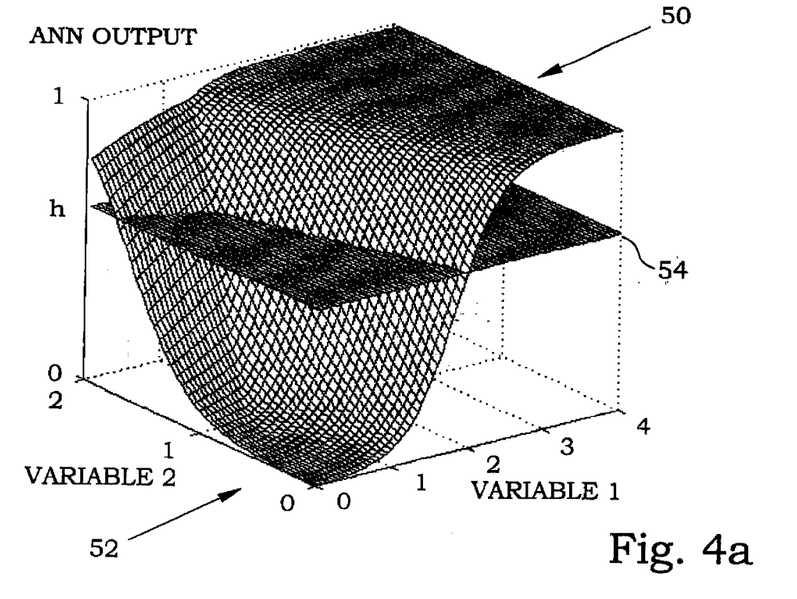
FIG. 4a is an illustration of the generation of decision regions according to the present invention.

One of the most essential parts of the first aspect of the present invention is the generation and visualization of decision regions, as described briefly above. In conventional artificial neural network use for classification, the artificial neural network creates an output y, which is compared with a threshold value. If the output is above the threshold a certain classification is selected, otherwise another classification is selected. As illustrated in FIG. 4a, the artificial neural network according to the present invention instead calculates decision regions. In FIG. 4a, the regions are expressed by means of two variable coordinates, whereby an output y from the artificial neural network is dependent on the two variables, i.e. an output $y(v_1, v_2)$. The different decision regions are then determined by the relation $y(v_1, v_2) > h$, where h is a threshold value. This threshold value is indicated as the plane 54 drawn in FIG. 4a. From the figure, it is easily distinguishable that one region 52 is present in the lower left corner, where the surface corresponding to $y(v_1, v_2)$ is positioned below the threshold plane 54, and another decision region 50 is present to the right and/or in the upper part, where the surface is present above the threshold plane 54. A measurement of $v_1$ and $v_2$ then corresponds to a certain point in the $v_1$–$v_2$ plane, and is therefore related to one of the regions. The closeness of the point position to the border of the decision region gives some hints about how accurate the assignment of decision region is.

Figure 4B:
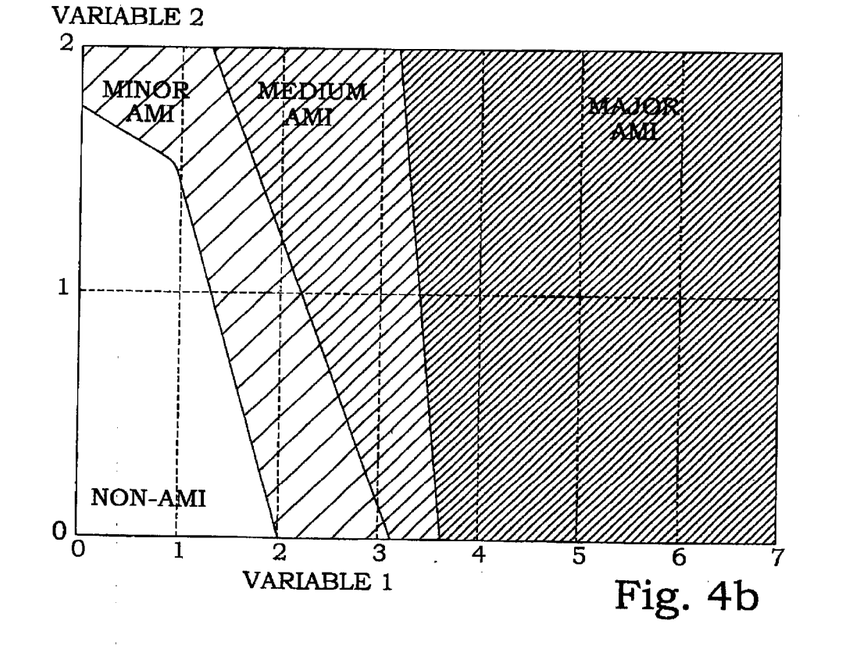
FIG. 4b is an illustration of the visualization of decision regions according to the present invention.

In use of a decision algorithm based on three artificial neural networks for classification and visualization of a patient in terms of "non-AMI", "minor AMI", "medium AMI" and "major AMI", the corresponding decision regions are illustrated in FIG. 4b. The decision regions are here projected onto the $v_1$–$v_2$-plane. The point corresponding to the actual measurement may be presented graphically in this diagram, together with e.g. its 95% confidence limits. The position and distance to neighboring decision regions are then easily interpreted as a classification and uncertainty, respectively, and used as a decision support.

Mathematically, the procedure can be expressed in the following manner. An artificial neural network model $y = g(x, \theta)$, where $x = [x_{01} \ldots x_1]$ is the input vector of the set of I input variables and the adjustable parameters (weights and bias) are represented by $\theta = [w_0 w_1 \ldots w_1]$ ($x_0 = 1$ to conveniently denote any bias term as $w_0$), can be utilized in a decision rule d by defining a decision threshold $h_{dec}$:

$$d = \begin{cases} \text{"rule-in"}, & \text{if } y \geq h_{dec} \\ \text{"rule-out"}, & \text{if } y < h_{dec} \end{cases}$$

When an artificial neural network is used for ruling-in or ruling-out of patient conditions that are developing during the course of measurements, timed measurements are analyzed. The decision rule d may then be modified so that $h_{dec}$ is the decision threshold with which the ANN output value is compared, and $t_{mon}$ is a predefined monitoring time. If the output exceeds $h_{dec}$, a positive classification ("ruling-in") is generated. Otherwise, the current measurement time is compared to $t_{mon}$. If the current time is greater than $t_{mon}$, a negative classification ("ruling-out") is generated, while if it is less than $t_{mon}$, the ANN algorithm indicates that a definitive classification can not yet be generated, and recommends further measurements to be performed.

The decision region boundaries are hyperplanes $h_{dec} = g(x, \theta)$ in the I-dimensional input AMI-variable/parameter space, and define decision regions with the two AMI categories.

Figure 2C:
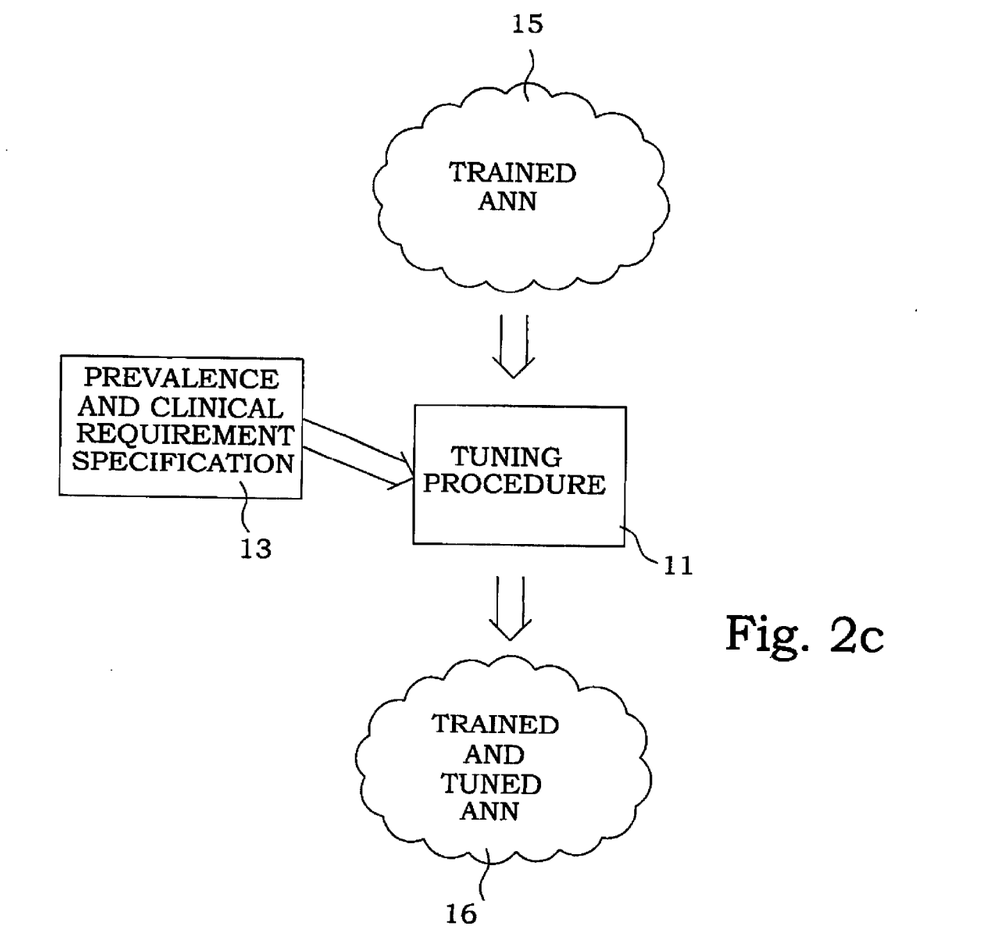
FIG. 2c is a schematic illustration of a tuning procedure of an artificial neural network used in the present invention.

A trained artificial neural network should in general be tuned to give an acceptable performance in the actual environment where it is going to be used. An artificial neural network, trained with a certain set of measurements is put through a tuning procedure (c.f. FIG. 2c).

According to a second aspect of the invention, the classifications produced by the ANN-based decision algorithm (ANN algorithm) can be tuned in order to meet medical requirements specified at the site of usage. These requirements are expressed as required minimal positive and negative predictive values given the current prevalence of disease. It is achieved by careful determination of the two parameters in the ANN algorithm, $h_{dec}$ and $t_{mon}$.

A basic calculation that will be used in the forthcoming procedure is the determination of the threshold parameter $h_{dec}$ so that the ANN algorithm performs classifications with a certain desired "tuned level of specificity", $spec_{tuned}$, for a fixed monitoring period $t_{mon}$. It is determined as follows:

$$h_{dec} = \arg\min_h \{spec(t_{mon}, h) \geq spec_{tuned}\} \quad (1)$$

where spec(t,h) represents cumulated specificity calculated on the training set at time t after start of measurements using threshold h.

The procedure for setting the parameters $h_{dec}$ and $t_{mon}$ in the ANN decision algorithm so that the medical requirement specification is met, is as follows: The prevalence of the pathological condition (e.g. AMI) must be known, and the clinical requirements for maximal monitoring time $t_{mon}$ and minimum positive and negative predictive values must be specified to start with. The ANN algorithm is then tuned to different specificities in the interval of clinical interest e.g. $spec_{tuned} = (0.80 \ldots 1.00)$ using eq. (1). Each level of tuned specificity results in a corresponding value of $h_{dec}$. Actual diagnostic sensitivities and specificities for consecutive measurements are then calculated using the results of the ANN algorithm when applied to an independent test set. This is performed for all levels of "tuned specificity".

By using the a priori known prevalence of the disease and the calculated actual diagnostic specificities and sensitivities for the tuned specificities, the corresponding actual positive and negative predictive values corresponding to each of these selected tuned specificities can be calculated as well. In order to select a good compromise between positive and negative predictive values, the predictive values are preferably plotted as functions of specificity. From this plot and the medically required minimal predictive values, an "optimal" level of tuned specificity is determined. This directly gives the corresponding $h_{opt}$. Following the outlined procedure, the parameters of the ANN algorithm are determined in such a way that the diagnostic performance fulfils clinically relevant requirements on predictive values. If the performance is not acceptable for any level of specificity, $t_{mon}$ has to be increased, which results in increased diagnostic performance at the price of a longer monitoring time. The above steps are then repeated.

Figure 5:
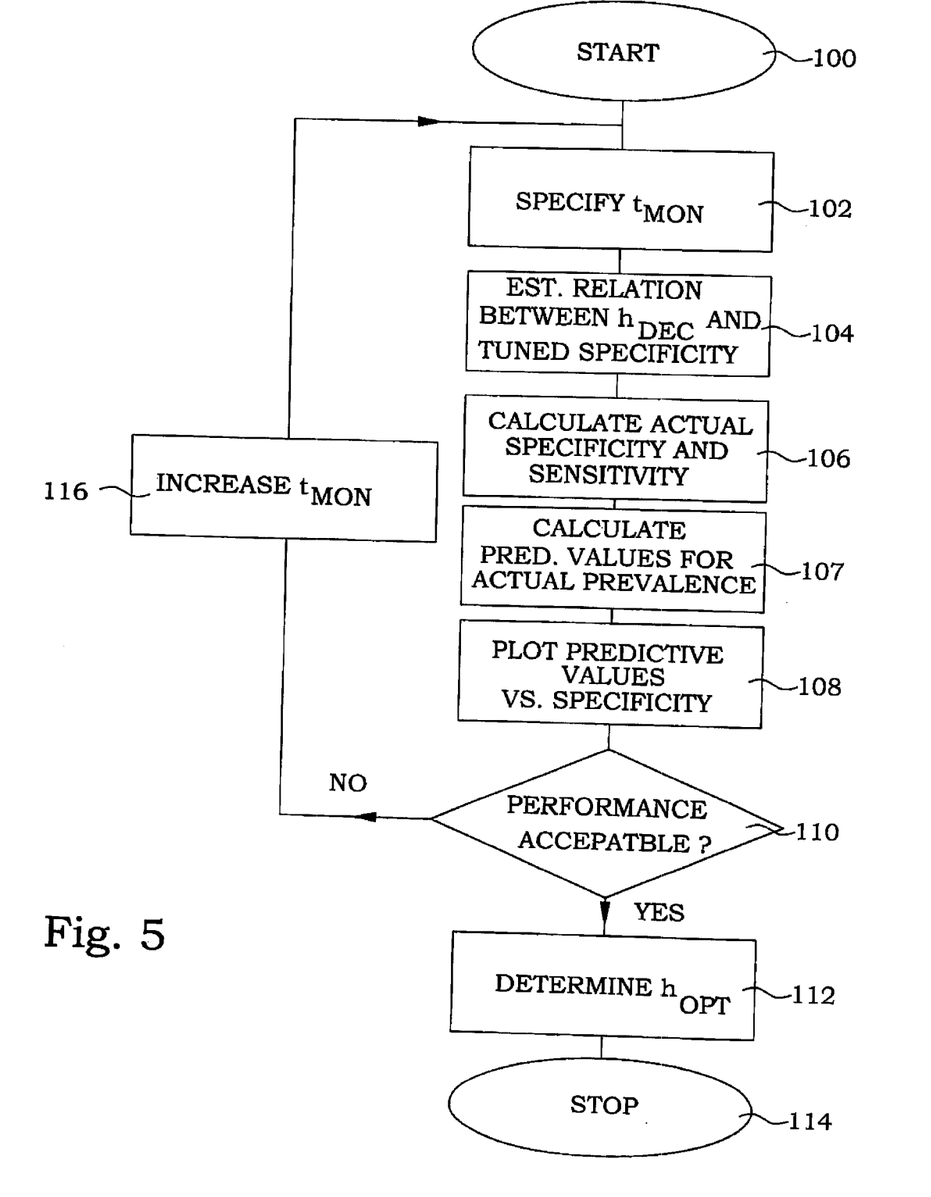
FIG. 5 is a flow diagram illustrating the tuning procedure.

The above tuning procedure can be illustrated by the flow diagram of FIG. 5. The procedure starts in step 100. In step 102, the mamal monitoring time $t_{mon}$ is specified. A relationship between tuned specificity and $h_{dec}$ is established in step 104. In step 106, a test set is used to calculate actual specificity and sensitivity. In step 107, corresponding actual predictive values are calculated for the actual prevalence, using the test set. The predictive values are plotted as functions of specificity in step 108, and from this plot and clinical requirements on predictive values, it is decided in step 110 if the requirements are possible to fulfil. If the requirements are not fulfilled, the procedure continues to step 116, where $t_{mon}$ is increased. The whole procedure then starts all over again from step 102. If the requirements are possible to fulfil, an optimal value $h_{opt}$ is determined in step 112. The procedure is ended in step 114.

Figure 6:
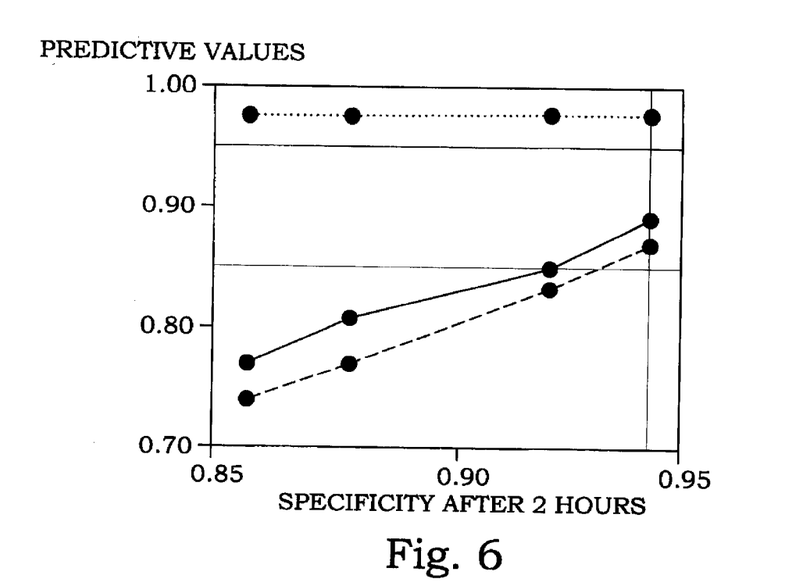
FIG. 6 is a diagram used in the tuning procedure according to the present invention.

For further illustration, see FIG. 6. Positive predictive value on admission PPV0 h is represented by the solid line, positive predictive value after two hours PPV2 h is represented by the broken line and negative predictive value after two hours NPV2 h is represented by the dotted line. Here the prevalence of AMI was set equal to 0.30 and the maximal monitoring time $t_{mon}$ was set equal to 2 hours. It is further assumed that a positive predictive value on admission PPV>0.85 and a negative predictive value after two hours NPV>0.95 as clinically required (represented by the thin solid horizontal lines in FIG. 6). According to FIG. 6, the required diagnostic performance is achieved in this case by selecting a high level of specificity equal to 0.94, which corresponds to PPV0 h=0.89, PPV2 h=0.88 and NPV2 h=0.98 after tuning of the ANN-decision algorithm.

Each set of variables used either to produce relevant decision regions, or to span the space in which the decision regions are expressed, is associated with a certain time instance. This time "label" is of special importance for the training of the artificial neural network. The ideal time would be the time that has elapsed since the start of the infarction process. However, since this to is unknown, the time since the onset of symptoms of a possible AMI is used as a time reference. Another time reference in presentation of results is the time from start of measurements, usually admission time.

According to a third aspect of the invention, the AMI variables used in the trained and tuned artificial neural network are not only selected from biochemical markers of AMI, but also from variables derived from intermittent/continuous ECG/VCG recordings.

The general advantages for use of biochemical markers is described in U.S. Pat. No. 5,690,103. Concentration levels of biochemical markers of AMI are measured in circulating blood of a patient. In practice, a blood sample is collected, and may also be separated into different fractions, such as plasma, blood corpuscles or platelets. Biochemical markers, which follow the plasma, are then measured. Preferably, the first measurement of concentration levels is performed on admission of the patient. It should be understood that hereinafter the expression measurement of concentrations of biochemical markers generally means the whole process of taking blood samples and analyzing the samples to determine the concentration levels of the biochemical AMI-markers.

There are important differences in the properties of the biochemical markers of AMI of today, e.g. myoglobin, CK-MB and cardiac troponin-T. The used biochemical markers are preferably selected such that they have different rates of appearance in plasma after an AMI. An increase of myoglobin mass concentration can be measured in plasma already after 1–2 hours after the infarct onset, while CK-MB and troponin-T starts to increase after 3–4 hours. Troponin-T remains elevated up to three weeks after an AMI, while CK-MB remains elevated for 2–3 days and myoglobin for one day. For all three markers the diagnostic sensitivity for AMI is high. A minor elevation of troponin-T and CK-MB, indicating minor myocardial damage, can be detected in at least 30% of all patients with the diagnosis of unstable angina according to conventional criteria. Myoglobin has a poor diagnostic specificity since myoglobin is also released from damaged skeletal muscles. Other biochemical markers, which are of interest in connection of AMI, are e.g. troponin I, glycogen phosphorylase BB, lactate dehydrogenase, and heart-type fatty acid binding protein (h-FABP).

Most departments dealing with patients with suspected AMI today apply intermittent or continuous ECG or VCG recordings. Initial ECG is commonly used for ruling-in of AMI. However, most of the patients arriving with chest pain do not present with a diagnostic initial ECG. In prior art, ruling-in/ruling-out of these patients depend on repeated measurements of biochemical AMI markers. However, properly pre-processing of ECG/VCG recordings may provide derived AMI parameters and time-stamped AMI variables that can be used in addition to biochemical AMI variables to improve the performance of ANN algorithms. Example of derived ECG parameters/variables which are candidates for contributing to the ANN performance are the sum of R-wave amplitudes, maximal ST-depression and mean R-wave duration in anterior leads.

The ECG/VCG variables may easily be used as the above described "additional" variables, but could in principle also appear as the variables corresponding to the coordinates for the decision regions.

Depending on the specific application, there are different optimal choices of the type of artificial neural network. In a system using only biochemical AMI variables, single- or multiple-single-layer perceptrons are good choices. When patient specific parameters are involved, a fuzzified single-layer perceptron might be a good candidate for the artificial neural network. The different networks are briefly described below. Anyone skilled in the art understands that ANNs other than the above mentioned also may be used in the present invention.

The single-layer perceptron (SLP), also denoted logistic regression, is a non-linear model with a linear decision boundary in the input vector space. The output value y is given by $$y = F\left(\sum_{i=0}^{I} w_i x_i\right)$$

$$F(\phi) = \frac{1}{1 + \exp(-\phi)}$$

where $x=[x_0 x_1 \ldots x_I]$ is the input vector (with $x_0=1$ to conveniently denote the bias term as $w_0$), and $x_1 \ldots x_I$ is the set of I input variables. The adjustable parameters (weights and bias) are represented by $\theta=[w_0 w_1 \ldots w_I]$. F is a sigmoidal function with a value range (0,1).

The single-layer perceptron with fuzzified input variables (FSLP), is an SLP with the addition that the input variables are unvariately pre-processed with use of sigmoidal membership functions in order to achieve non-linear classification. The fuzzifying membership functions are given by $$f(x_i) = \frac{1}{1 + e^{-\beta_i(x_i - \alpha_i)}} \quad 0 \leq f(x_i) \leq 1, i = 1, \ldots I$$

where $\alpha_i$ positions, and $\beta_i$ determines the width of the sigmoidal function. $\alpha_i$ equals the value of $x_i$ for which $f(x_i)$ is 0.5, while a larger $\beta_i$ makes the separation between the two classes (AMI and non-AMI) more distinct. The values of the parameters $\alpha_i$ are determined independently for the input variables $x_i$ so that the number of misclassified cases is minimized when used as a univariate decision level for $x_i$. The $\beta_i$ parameters are determined by systematic variation. This model can be used with $\alpha_i$ and $\beta_i$ included as parameters in the objective function to be estimated simultaneously with weights and biases automatically in the training process.

The multiple-single-layer perceptron (m:MSLP) refers to a structure where m "expert" SLPs are used in parallel. Each SLP is trained on a selected partition of the training set where the measurements of markers all come from e.g. the same time interval since onset of infarction. The output of the m:MSLP is defined as the maximum of the outputs from the individual SLps $$y=\max(y_1, y_2, \ldots, y_m)$$

When designing a decision support system (DSS), a combination of different ANN algorithms may be used.

In order to facilitate the understanding of the fundamental ideas of the present invention, an exemplifying embodiment will be described more in detail, together with results obtained by such an embodiment.

Figure 7:
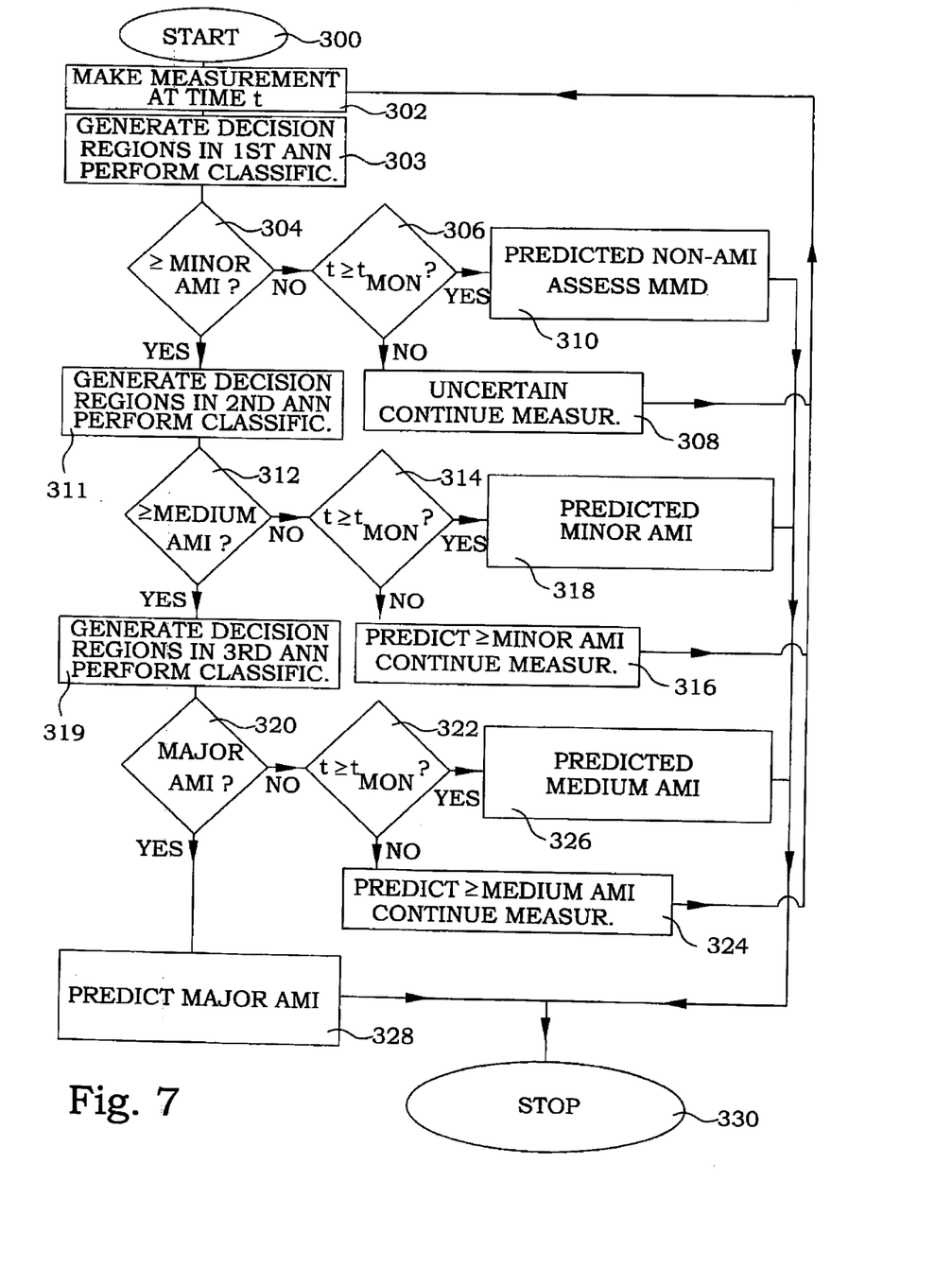
FIG. 7 is a flow diagram illustrating a combined decision procedure according to one embodiment of the present invention.

Three trained and tuned ANN-based decision algorithms (MSLP, SLP and SLP) were combined to form a key component of a decision support system (DSS) in order to generate predictions of "non-AMI", "minor AMI", "medium AMI" and "major AMI". FIG. 7 is a top-level diagram displaying computational processes. The procedure starts in step 300. The process 302 represents timed measurements of infarct markers in plasma from a patient with chest pain and non-diagnostic ECG on admission. These measurements can be performed with use of commercially available decentralized instruments with sufficiently short turn-around time for analysis, preferably less than 20 min. The results of these measurements, plasma-mass concentration values of myoglobin and CKMB, are taken as input values to the first ANN for generating decision regions and perform classification 303 with regard to "at least minor AMI" 304. If a negative indication is generated, the current time t is compared to the required monitoring time $t_{mon}$ 306. If $t \geq t_{mon}$, a prediction of Non-AMI is generated 310. If however $t < t_{mon}$, the DSS indicates "uncertainty" 308, requiring further measurements to be performed. If the first ANN generated a positive indication of "At least Minor AMI" as decided in step 304, a new classification is performed using the second ANN that generates decision regions and performs classification 311 with regard to "At least Medium AMI" 312. If a negative indication is generated, the current time t is compared to the required monitoring time $t_{mon}$ 314. If $t \geq t_{mon}$, a prediction of minor AMI is generated 318. If however $t < t_{mon}$, the DSS predicts "At least minor AMI" 316, requiring further measurements to be performed. If the ANN generated a positive indication of "At least Medium AMI" as decided in step 312, a new classification is performed using the third ANN that generates decision regions and performs classification 319 with regard to "Major AMI". If a negative indication is generated, the current time t is compared to the required monitoring time $t_{mon}$ 322. If $t \geq t_{mon}$, a prediction of medium AMI is generated 326. If however $t < t_{mon}$, the DSS predicts "At least medium AMI" 324, requiring further measurements to be performed. If the third ANN generated a positive indication of "Major AMI" as decided in step 320, major AMI is predicted in step 328 and the procedure is ended in step 330. All steps are ended when $t \geq t_{mon}$ and the total procedure is ended in step 330.

According to the present invention, the marker concentrations are plotted in the P-Myoglobin—P-CKMB plane. Decision regions generated by the three ANN-based decision algorithms are superimposed on such a plot to achieve a graphical presentation of the predictions generated by the DSS. The regions generated using time from onset in the set of input variables makes it necessary to generate decision regions for each measurement. The normalized marker values (i.e. values divided by their respective upper reference limits for healthy individuals, URL) can be plotted in such a graph together with their respective 95% confidence limits, giving the user a possibility to estimate how certain the system is in its predictions, from the position of the measurement point in relation to the boundaries of the decision regions.

Figure 8A:
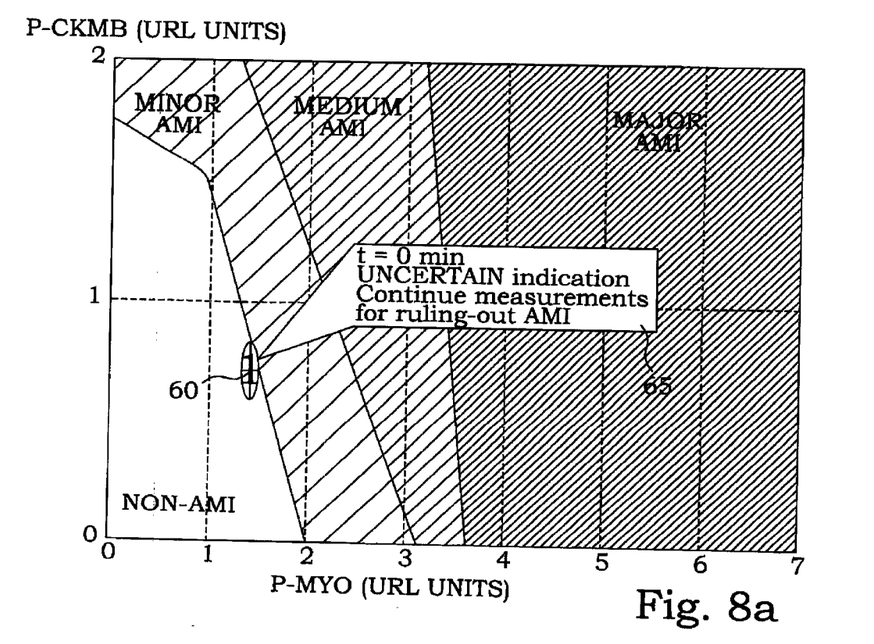
FIGS. 8a–c are examples of graphical visualizations of decision regions at different stages of patient monitoring.
Figure 8B:
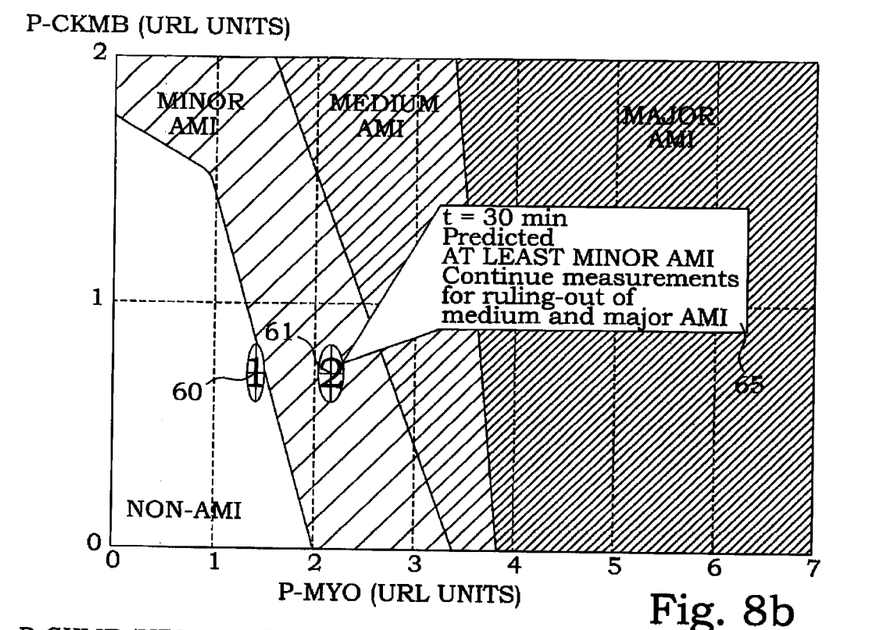
Figure 8C:
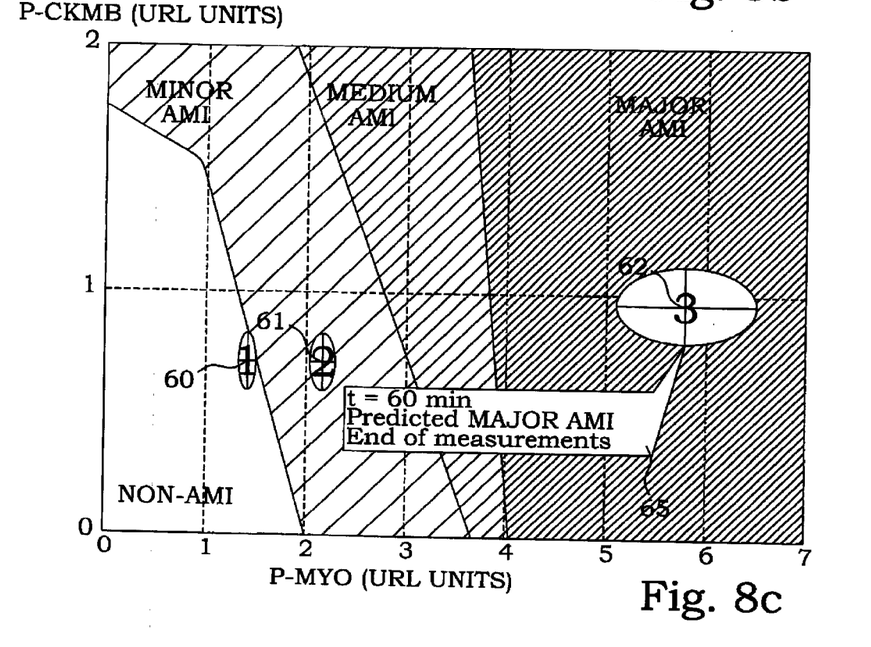

In FIGS. 8a to 8c, four decision regions are visualized as generated by the three ANN-based decision algorithms. The figures display three sets of successive measurements of P-Myoglobin and P-CKMB, normalized and plotted with their respective 95% confidence intervals. FIG. 8a illustrates the situation after the first measurement. The point 60 corresponding to the measured values of P-Myoglobin and P-CKMB of the first measurement set on admission of the patient appears within the region of "non-AMI" indication, but since the maximum monitoring time has not expired an "uncertain indication" is displayed and the measurements continue. Preferably, a text field 65 is provided, in which predictions, indications, measurement time (from admission) etc. are presented in writings. The measurement number is also preferably indicated in connection with the measurement point. In FIG. 8b, the situation at the second measurement 61 is illustrated. "At least minor AMI" was predicted after two sets of measurements. Since the maximum monitoring time was not reached, the measurements continued. FIG. 8c finally illustrates the situation when the third measurement 62 was made available, and "major AMI" was predicted. No further measurements were necessary. Note that since the time of the measurements are different, the decision region boundaries are modified between each of the measurements, i.e. the decision regions are dynamic and calculated for each individual patient and measurement time.

This way of representing the outputs generated by the combined ANN decision algorithms for prediction of infarct size helps explaining its reasoning.

Figure 9:
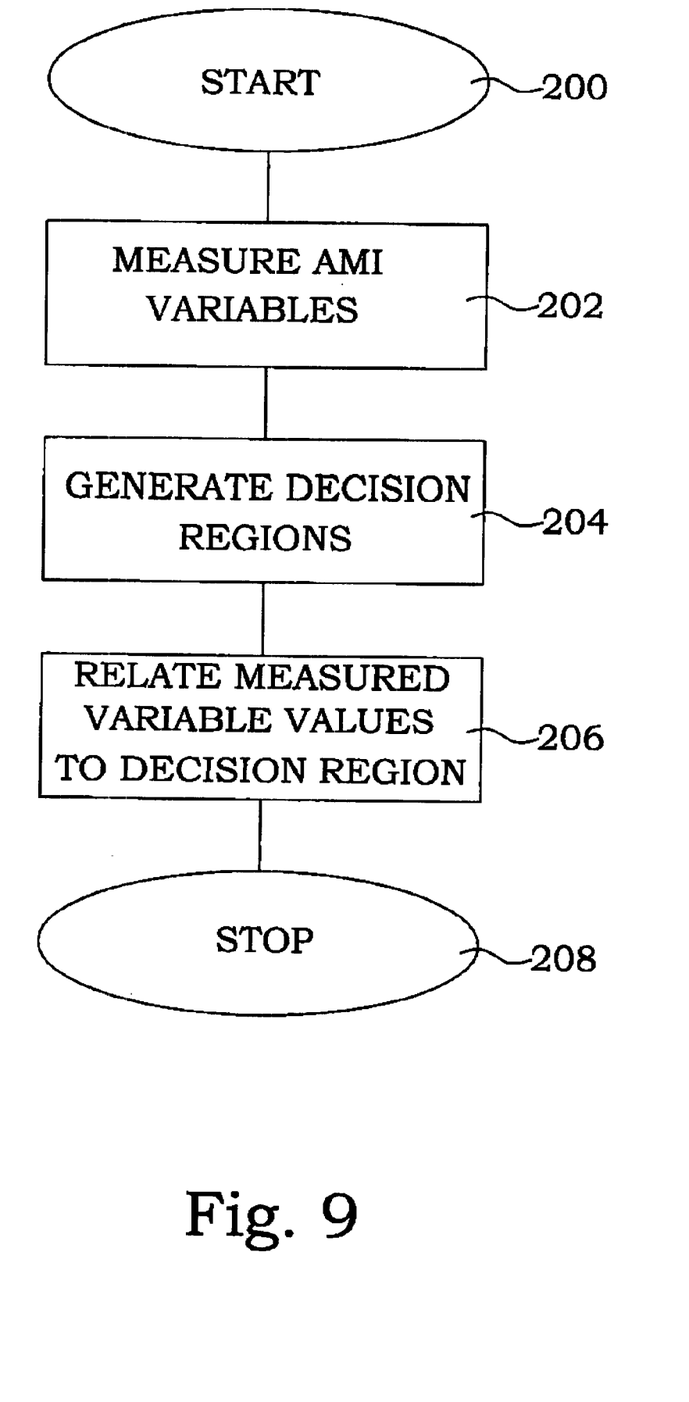
FIG. 9 is a flow diagram illustrating a procedure according to the present invention.

In FIG. 9, a flow diagram illustrates basic steps in the present invention. The procedure starts in step 200. In step 202, variables related to AMI are measured. Decision regions are generated by an artificial neural network in step 204. The measured variables are then in step 206 related to the generated decision regions, providing indication of acute myocardial infarction of various size. The procedure is ended in step 208.

It will be understood by those skilled in the art that various modifications and changes may be made to the present invention without departure from the scope thereof, which is defined by the appended claims.

What is claimed is:

1. A method of providing decision support for early assessment of patients with suspected acute myocardial infarction (AMI), comprising the steps of:

measuring a set of n variables related to AMI of a patient at at least one measuring time instance, where $n \geq 2$;

generating m decision regions, where $m \geq 2$, in the n-dimensional space of said n variables by means of at least one artificial neural network, trained on a training set of n measured variables from m classification groups of typical patients; and relating the values of said n variables of a present measurement set to said m decision regions in said n-dimensional space in order to indicate AMI characteristics.

2. The method according to claim 1, further comprising the step of:

graphically displaying same m decision regions and a number of said values of said n variables of said present measurement set.

3. The method according to claim 1, wherein said m decision regions correspond to AMI of different sizes.

4. The method according to claim 1, wherein said m decision regions correspond to different preferred management options and/or treatment procedures.

5. The method according to claim 1, wherein said variables related to AMI are selected from the list of:
   concentrations of biochemical markers of AMI in circulating blood of the patient; and
   derived quantities from intermittent/continuous ECG/VCG.

6. The method according to claim 5, wherein said biochemical markers are selected from the list of:
   myoglobin,
   creatine kinase MB,
   troponin T,
   troponin I,
   glycogen phosphorylase BB,
   lactate dehydrogenase, and
   heart-type fatty acid binding protein (h-FABP).

7. The method according to claim 1, further comprising the step of:
   providing the time instance of the present measurement set relative to time from onset of symptoms to said artificial neural network/networks, said artificial neural network/networks being further trained with said relative onset time instances of measurement sets of said n variables as an additional input variable, whereby said step of generating decision regions is further based on the relative onset time instance of the present measurement set.

8. The method according to claim 7, further comprising the step of:
   providing patient-specific parameters to said artificial neural network/networks, said artificial neural network/networks being her trained with patient-specific parameters, whereby said step of generating decision regions is further based on said patient-specific parameters.

9. The method according to claim 8, wherein at least one of said patient-specific parameters is selected from the list of:
   derived quantities from initial ECG/VCG,
   sex of the patient,
   patient age,
   risk factors of AMI,
   present patient health status, and
   earlier history of diseases.

10. The method according to claim 2, wherein
   said m decision regions are displayed in a k-dimensional diagram defined by coordinates of k of said variables,
   the values of said k variables of said present measurement set are displayed as a point in said k-dimensional diagram, and
   the remaining n−k variable values are used for generating said decision regions.

11. The method according to claim 10, wherein k=2.

12. The method according to claim 1, wherein said artificial neural network(s) is(are) of a type selected from the list of:
   single-layer perceptron,
   multiple-single-layer perceptron, and
   single-layer perceptron with fuzzified input variables.

13. The method according to claim 10, wherein confidence regions of said values of said k variables of said present measurement set are displayed as an area in said k-dimensional diagram.

14. The method according to claim 1, further comprising the step of:
   tuning the performance of said artificial neural network/networks to clinical requirements on predictive values of output in given prevalence situations.

15. A method of providing decision support for early assessment of patients with suspected acute myocardial infarction (AMI), comprising the steps of:
   measuring a set of n variables related to AMI of a patient at at least one measuring time instance, where $n \geq 2$;
   generating a classification of said patient by means of at least one artificial neural network, trained on a training set of n measured variables from m classification groups of typical patients, where $m \geq 2$; and
   where at least one of said variables related to AMI is a derived quantity from intermittent/continuous ECG/VCG.

16. A method of providing decision support for early assessment of patients with suspected acute myocardial infarction (AMI), comprising the steps of:
   measuring a set of n variables related to AMI of a patient at at least one measuring time instance, where $n \geq 2$;
   generating a classification of said patient by means of at least one artificial neural network, trained on a training set of n measured variables from classification groups of typical patients; and
   tuning the performance of said artificial neural network/networks to clinical requirements on predictive values of artificial neural network output in given prevalence situations.

17. A device for providing decision support for early assessment of patients with suspected acute myocardial infarction (AMI), comprising:
   at least one artificial neural network, trained on a training set of n measured variables related to AMI from m classification groups of typical patients, and arranged for generating at least m decision regions in the n-dimensional space of said n variables, where $n, m \geq 2$;
   means for inputting a present set of n measured values of variables related to AMI of a patient from at least one measuring time instance;
   means for relating said n values of said present measurement set to said m decision regions in said n-dimensional space for indicating AMI characteristics.

18. The device according to claim 17, further comprising:
   graphical means for visualizing said m decision regions and a number of said n values of said present measurement set.

19. The device according to claim 17, wherein said m decision regions correspond to AMI of different sizes.

20. The device according to claim 17, wherein said m decision regions correspond to different preferred management options and/or treatment procedures.

21. The device according to claim 17, wherein said variables related to AMI are selected from the list of:
   concentrations of biochemical markers of AMI in circulating blood of the patient; and
   derived quantities from intermittent/continuous ECG/VCG.

22. The device according to claim 21, wherein said biochemical markers are selected from the list of:
   myoglobin,
   creatine kinase MB,
   troponin T,
   troponin I,
   glycogen phosphorylase BB,
   lactate dehydrogenase, and
   heart-type fatty acid binding protein (h-FABP).

23. The device according to claim 17, further comprising:
means for providing the time instance of the present measurement set relative to time from onset of symptoms to said artificial neural network/networks, said artificial neural network/networks being further trained with relative onset time instances of measurement sets of said n variables, whereby the generation of decision regions of said artificial neural network is further based on the relative onset time instance of the present measurement set.

24. The device according to claim 23, further comprising:
means for providing patient-specific parameters to said artificial neural network/networks, said artificial neural network/networks being further trained with patient-specific parameters, whereby the generation of decision regions of said artificial neural network is further based on said patient-specific parameters.

25. The device according to claim 24, wherein at least one of said patient-specific parameters is selected from the list of:
derived quantities from initial ECG/VCG,
sex of the patient,
patient age,
risk factors of AMI,
present patient health status, and
earlier history of diseases.

26. The device according to claim 18, wherein said graphical means comprises
means for visualizing said m decision regions in a k-dimensional diagram defined by coordinates of k of said variables,
means for visualizing the values of said k variables of said present measurement set as a point in said k-dimensional diagram, and said artificial neural network/networks is/are arranged for generating said m decision regions based on the remaining n–k variable values.

27. The device according to claim 26, wherein k=2.

28. The device according to claim 17, wherein said artificial neural network(s) is(are) of a type selected from the list of:
single-layer perceptron,
multiple-single-layer perceptron, and
single-layer perceptron with fuzzified input variables.

29. The device according to claim 26, wherein said graphical means comprises means for visualizing confidence regions of said values of said k variables of said present measurement set as an area in said k-dimensional diagram.

30. The device according to claim 17, further comprising:
means for tuning the performance of said artificial neural network/networks to clinical requirements on predictive values of output in given prevalence situations.

31. A device for providing decision support for early assessment of patients with suspected acute myocardial infarction (AMI), comprising:
at least one artificial neural network, trained on a training set of n measured variables related to AMI from m classification groups of typical patients, and arranged for classifying said patient, where n, m$\geq$2;
means for inputting a set of said n measured values related to AMI of a patient from at least one measuring time instance; and
where at least one of said variables related to AMI is a derived quantity from intermittent/continuous ECG/VCG.

32. A device for providing decision support for early assessment of patients with suspected acute myocardial infarction (AMI), comprising:
at least one artificial neural network, trained on a training set of n measured variables related to AMI from m classification groups of typical patients, and arranged for classifying said patient, where n, m$\geq$2;
means for inputting a present set of said n measured values related to AMI of a patient from at least one measuring time instance to generate a classification of said patient; and
means for tuning the performance of said artificial neural network/networks to clinical requirements on predictive values of output in given prevalence situations.

* * * * *